(12) United States Patent
Kim (10) Patent No.: US 8,800,377 B2
(45) Date of Patent: Aug. 12, 2014

(54) CONTACT FORCE SENSOR PACKAGE, BLOOD PRESSURE METER WITH THE SAME, AND METHOD FOR FABRICATING THE CONTACT FORCE SENSOR PACKAGE

(75) Inventor: Jong-pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1611 days.

(21) Appl. No.: 12/055,337

(22) Filed: Mar. 26, 2008

(65) Prior Publication Data

US 2009/0177096 A1 Jul. 9, 2009

(30) Foreign Application Priority Data

Jan. 4, 2008 (KR) .................. 10-2008-0001429

(51) Int. Cl.
*G01L 9/06* (2006.01)
*A61B 5/021* (2006.01)

(52) U.S. Cl.
CPC ......... *A61B 5/021* (2013.01); *A61B 2562/0247* (2013.01)
USPC .................. 73/727; 73/753; 73/754; 128/897

(58) Field of Classification Search
None
See application file for complete search history.

(56) References Cited

U.S. PATENT DOCUMENTS 5,179,956 A * 1/1993 Harada et al. ............... 600/485
7,584,666 B2 * 9/2009 Kim et al. .................... 73/727

FOREIGN PATENT DOCUMENTS

| JP | 06232204 | 8/1994 |
| JP | 08064636 | 3/1996 |
| JP | 2002231760 A | 8/2002 |
| JP | 2007047023 A | 2/2007 |

OTHER PUBLICATIONS

Communication, dated Mar. 26, 2014, issued by the Korean Intellectual Property Office in counterpart Korean Patent Application No. 10-2008-0001429.

* cited by examiner

*Primary Examiner* — Shafiqul Haq (74) *Attorney, Agent, or Firm* — Sughrue Mion, PLLC (57) ABSTRACT

A contact force sensor package includes a substrate layer having a vibration detection unit and a pair of first junction pads that are electrical connection ports which are provided on an upper surface of the substrate layer, a flexible circuit substrate layer having a pair of second junction pads provided at a position corresponding to the first junction pads and electrically connected to the first junction pad, a vibration transfer unit having one side contacting the vibration detection unit and the other side contacting a human body and transferring a sphygmus wave of the human body to the vibration detection unit, and an adhesion layer formed between the substrate layer and the flexible circuit substrate layer to reinforce a junction force between the substrate layer and the flexible circuit substrate layer, the adhesion layer being not formed in an area overlapping at least the vibration transfer unit.

19 Claims, 9 Drawing Sheets

CONTACT FORCE SENSOR PACKAGE, BLOOD PRESSURE METER WITH THE SAME, AND METHOD FOR FABRICATING THE CONTACT FORCE SENSOR PACKAGE

CROSS-REFERENCE TO RELATED PATENT APPLICATIONS

This application claims the benefit of Korean Patent Application No. 10-2008-0001429, filed on Jan. 4, 2008, in the Korean Intellectual Property Office, the disclosure of which is incorporated herein in its entirety by reference.

BACKGROUND OF THE INVENTION

1. Field of the Invention

The present invention relates to a contact force sensor package for detecting the sphygmus wave of a human body to measure blood pressure, blood pressure meter with the contact force sensor package, and a method for fabricating the contact force sensor package.

2. Description of the Related Art

A blood pressure meter is a device to measure blood pressure using the relationship between the blood pressure and a sphygmus wave according to the repeated contraction of a heart. The blood pressure meter includes a contact force sensor package.

Figure 1:
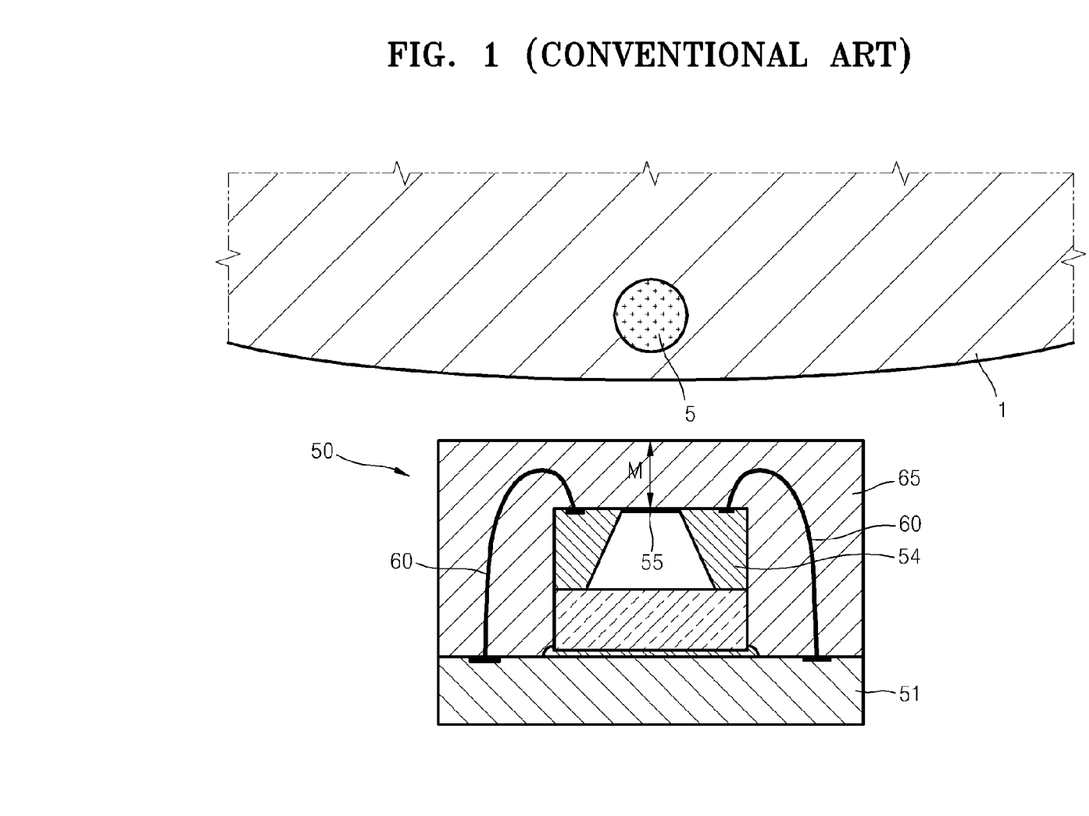
FIG. 1 is a cross-sectional view of an example of a typical contact force sensor package.

FIG. 1 is a cross-sectional view of an example of a typical contact force sensor package 50. Referring to FIG. 1, the contact force sensor package 50 contacts a wrist 1 where a radial artery 5 passes to detect a sphygmus wave. In the contact force sensor package 50, a substrate layer 54 having a thin film 55 is mounted on a circuit substrate layer 51 and the substrate layer 54 having the thin film 55 and the circuit substrate layer 51 are electrically connected via a bonding wire 60. To protect the bonding wire 60, the substrate layer 54 is sealed with an elastic material such as a silicon gel 65.

A vibration, that is, a sphygmus wave, generated from the radial artery 5 is transferred to the thin film 55 via the silicon gel 65. Accordingly, blood pressure is measured through a change of the thin film 55. However, since the bonding wire 60 that is tens of nanometers thick is weak to an impact, to prevent disconnection of the bonding wire 60 due to the vibration transferred to the silicon gel 65, the silicon gel 65 on the thin film 55 is formed to have a thickness M that is relatively thick.

For this reason, it is difficult to reduce the size of the contact force sensor package. Also, as the distance between the radial artery and the thin film increases, the sensitivity of detection of the sphygmus wave is deteriorated.

SUMMARY OF THE INVENTION

The present invention provides a contact force sensor package which can be manufactured to be compact and have an improved sphygmus wave detection sensitivity, a blood pressure meter with the contact force sensor package, and a method for fabricating the contact force sensor package.

According to an aspect of the present invention, a contact force sensor package comprises a substrate layer having a vibration detection unit and a pair of first junction pads that are electrical connection ports which are provided on an upper surface of the substrate layer, a flexible circuit substrate layer having a pair of second junction pads provided at a position corresponding to the first junction pad and electrically connected to the first junction pad, a vibration transfer unit having one side contacting the vibration detection unit and the other side contacting a human body and transferring a sphygmus wave of the human body to the vibration detection unit, and an adhesion layer formed between the substrate layer and the flexible circuit substrate layer to reinforce a junction force between the substrate layer and the flexible circuit substrate layer, the adhesion layer being not formed in an area overlapping at least the vibration transfer unit.

The vibration transfer unit is formed of an elastic material.

The elastic coefficient of the vibration transfer unit is less than that of the vibration detection unit.

The vibration transfer unit includes a portion of the flexible circuit substrate layer combined to the vibration detection unit.

The contact force sensor package further comprises an anisotropic conductive layer to electrically connect the first and second junction pads, wherein the vibration transfer unit includes a portion of the anisotropic conductive layer contacting the vibration detection unit and a portion of the flexible circuit substrate layer contacting the portion of the anisotropic conductive layer.

The flexible circuit substrate layer includes an opening formed to expose the vibration detection unit, and the vibration transfer unit includes a vibration transfer member provided in the opening, contacting the vibration detection unit, and capable of covering the opening.

The vibration transfer member is formed of an elastic material.

The vibration transfer unit includes an outermost layer formed of an elastic material that is harmless to the human body.

The contact force sensor package further comprises a pair of metal bumps providing electric connection between the first and second junction pads.

The adhesion layer is formed as a liquid material implanted between the substrate layer and the flexible circuit substrate layer is cured.

The vibration detection unit includes a shape deformation element whose shape is changed by a contact force and the shape deformation element has piezoresistance, piezoelectricity, and capacitance, at least one of which measurably varies according to the contact force.

The shape deformation element is one of a thin film, a cantilever beam, and a bridge.

According to another aspect of the present invention, a blood pressure meter comprises a blood pressure measuring block having at least one contact force sensor package detecting a sphygmus wave of a human body and measuring blood pressure based on the detected sphygmus wave, and a contact maintaining device maintaining a state in which the blood pressure measuring block contacts the human body, wherein the contact force sensor package comprises a substrate layer having a vibration detection unit and a pair of first junction pads that are electrical connection ports which are provided on an upper surface of the substrate layer, a flexible circuit substrate layer having a pair of second junction pads provided at a position corresponding to the first junction pads and electrically connected to the first junction pads, a vibration transfer unit having one side contacting the vibration detection unit and the other side contacting a human body and transferring a sphygmus wave of the human body to the vibration detection unit, and an adhesion layer formed between the substrate layer and the flexible circuit substrate layer to reinforce a junction force between the substrate layer and the flexible circuit substrate layer, the adhesion layer being not formed in an area overlapping at least the vibration transfer unit.

The blood pressure block includes a plurality of the contact force sensor packages and, when one of the contact force sensor packages detects an effective sphygmus wave, blood pressure is measured based on the detected sphygmus wave.

According to another aspect of the present invention, a method for fabricating a contact force sensor package comprises preparing a substrate layer having a vibration detection unit and a pair of first junction pads that are electrical connection ports which are provided on an upper surface of the substrate layer, providing a flexible circuit substrate layer having a pair of second junction pads at a position overlapping the first junction pads, and electrically connecting the first and second junction pads, forming a vibration transfer unit having one side contacting the vibration detection unit and the other side contacting a human body and transferring a sphygmus wave of the human body to the vibration detection unit, and forming an adhesion layer by implanting and curing a liquid material between the substrate layer and the flexible circuit substrate layer to reinforce a junction force between the substrate layer and the flexible circuit substrate layer, wherein the liquid material is not implanted in an area overlapping the vibration detection unit.

The forming of the vibration transfer unit is performed at the same time when the flexible circuit substrate layer is mounted, or before or after the flexible circuit substrate layer is mounted.

The vibration transfer unit is formed of an elastic material.

The forming of the vibration transfer unit includes combining a portion of the flexible circuit substrate layer to the vibration detection unit.

Electrically connecting of the first and second junction pads and the forming of the vibration transfer unit are simultaneously performed, and the above method further comprises providing an anisotropic conductive layer between the flexible circuit substrate layer and the substrate to electrically connected the first and second junction pads, and pressing the flexible circuit substrate layer against the substrate layer to allow one side of the anisotropic conductive layer to contact the vibration detection unit and the other side of the anisotropic conductive layer to contact the flexible circuit substrate layer.

The method further comprises forming an opening in the flexible circuit substrate layer to expose the vibration detection unit, wherein the forming of the vibration transfer unit comprises providing a vibration transfer member in the opening that is capable of contacting the vibration detection unit and covering the opening.

The vibration transfer member is formed of an elastic material.

Electrically connecting of the first and second junction pads includes forming a pair of metal bumps that electrically connect the first and second junction pads.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

Figure 2:
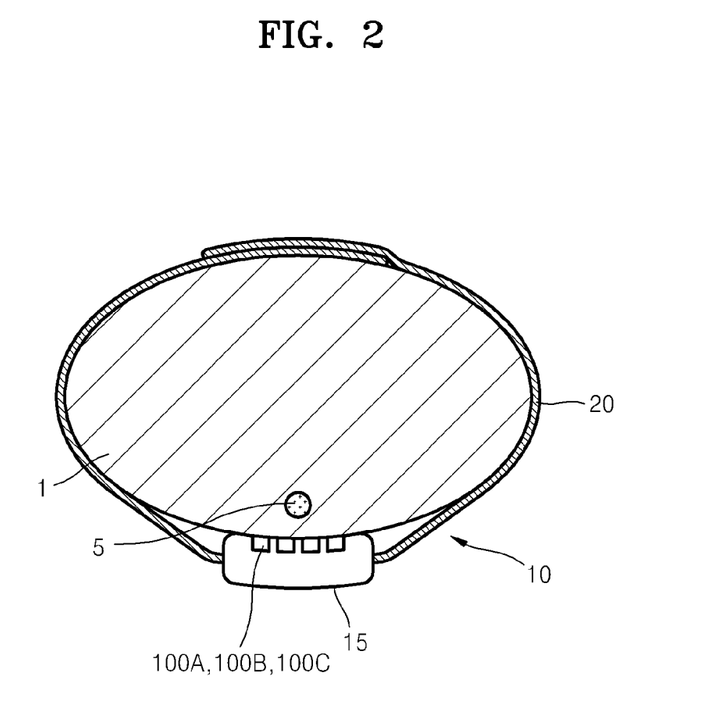
FIG. 2 is a cross-sectional view of a blood pressure meter according to an embodiment of the present invention.
Figure 3A:
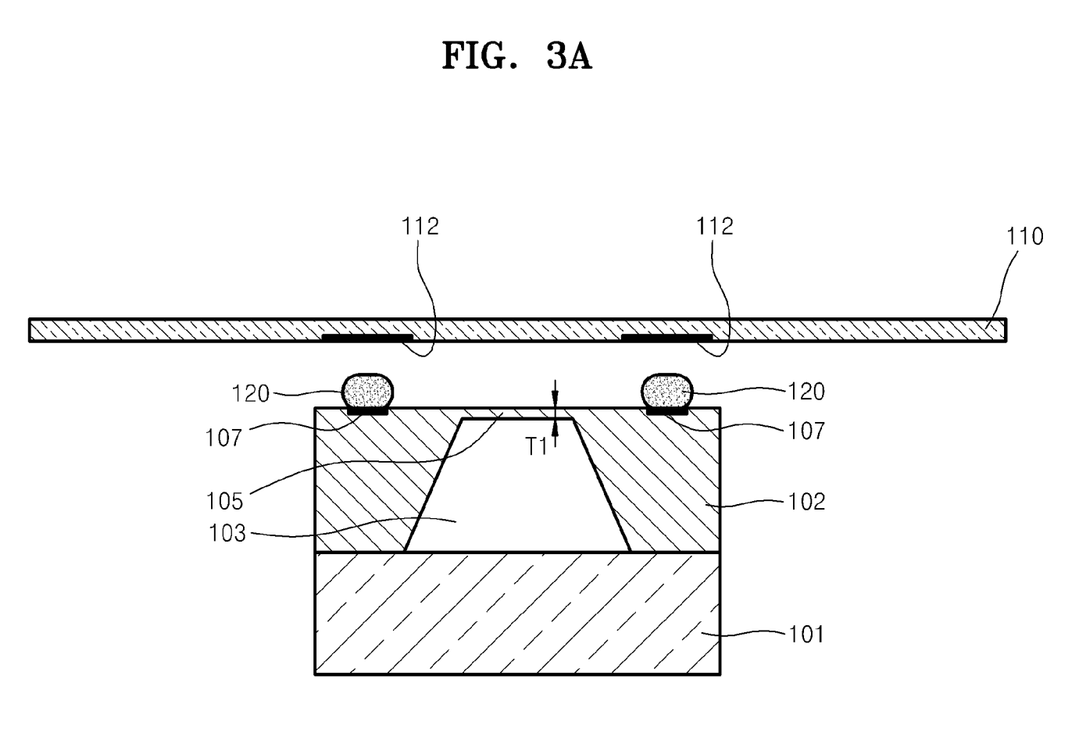
FIG. 3A is a cross-sectional view showing a method for fabricating a contact force sensor package according to an embodiment of the present invention.
Figure 3B:
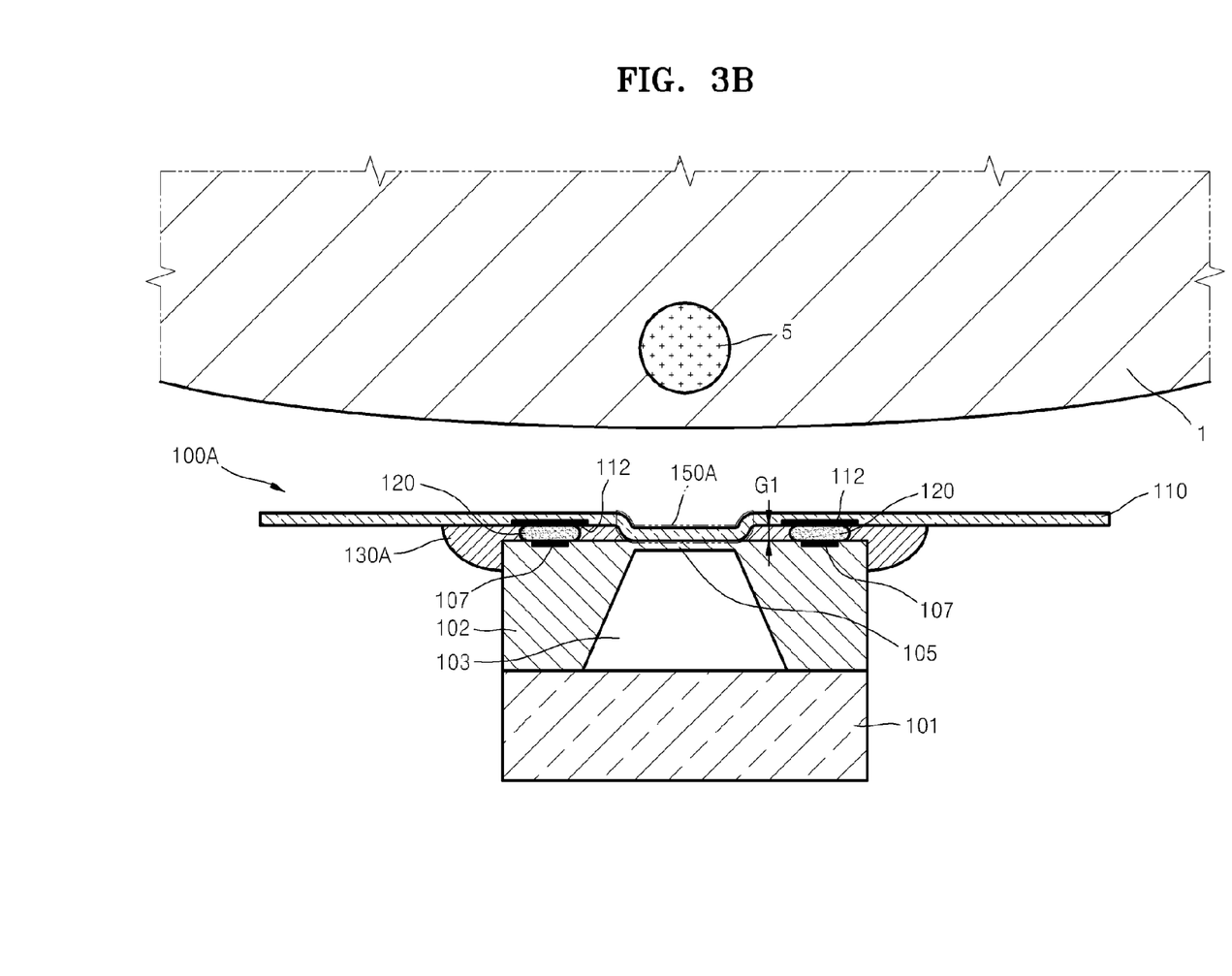
FIG. 3B is a cross-sectional view showing a completed contact force sensor package.

FIG. 2 is a cross-sectional view of a blood pressure meter 10 according to an embodiment of the present invention. FIG. 3A is a cross-sectional view showing a method for fabricating a contact force sensor package according to an embodiment of the present invention. FIG. 3B is a cross-sectional view showing a completed contact force sensor package.

Referring to FIG. 2, the blood pressure meter 10 according to the present embodiment is wearable on a wrist 1 where a radial artery 5 passes so that a sphygmus wave is easily detected, and includes blood pressure measuring block 15 measuring blood pressure and a contact maintaining device maintaining a state in which the blood pressure measuring block 15 contacts a human body, that is, the wrist 1. Although in the drawings the contact maintaining device includes a band 20 wrapping around the wrist, the present invention is not limited thereto. The blood pressure measuring block 15 includes a plurality of contact force sensor packages 100A detecting the sphygmus wave of a human body through the vibration of the radial artery 5, a processor (not shown) measuring blood pressure based on the detected sphygmus wave, and a display panel (not shown) visually indicating the measured blood pressure. The contact force sensor packages 100A are arranged close to one another in the minimum interval. When an arbitrary one of the contact force sensor packages 100A detects an effective sphygmus wave, the processor measures blood pressure based on the detected sphygmus wave.

Referring to FIGS. 3A and 3B, each of the contact force sensor packages 100A includes a base layer 101, a substrate layer 102 deposited on the base layer 101, a flexible circuit substrate layer 110 mounted on the substrate layer 102, and an adhesion layer 130A to reinforce a junction force between the substrate layer 102 and the flexible circuit substrate layer 110.

In the present embodiment, the base layer 101 is formed of glass and the substrate layer 102 is formed of silicon (Si). The substrate layer 102 includes a vibration detection unit and a pair of first junction pads 107 that are electric connection ports, on an upper surface of the substrate layer 102. The vibration detection unit includes a shape deformation element having a shape varying according to an applied contact force. The shape deformation element has piezoresistance, piezoelectricity, and capacitance, at least one of which measurably varies according to the contact force. In the present embodiment, the shape deformation element is a thin film 105. The thin film 105 is an example of the shape deformation element and a cantilever beam or a bridge can be adopted as the shape deformation element.

A cavity 103 forming the thin film 105 is formed in the substrate layer 102. As the thin film 105 vibrates, piezoresistive resistance that is sensitive to the strain of the thin film 105 varies. By applying a known current or voltage to thin film 105, a change in the voltage or current can be detected. Thus, the vibration of the thin film 105 due to the sphygmus wave can be detected through the change of the voltage or current.

In a method for fabricating the contact force sensor package 100A, as shown in FIG. 2A, the substrate layer 102 is prepared and deposited on the base layer 101. Next, the flexible circuit substrate layer 110 having a pair of second junction pads 112 is arranged at a position corresponding to the first junction pads 107. The flexible circuit substrate layer 110 is mounted on the substrate layer 102 by electrically and one to one connecting the first junction pads 107 and the second junction pads 112. The flexible circuit substrate layer 110 transfers an electric signal formed by detecting the sphygmus wave to the processor (not shown) of the blood pressure measuring block 15 of FIG. 2. The flexible circuit substrate layer 110 also protects the thin film 105 that is easily breakable by foreign materials and impacts such as scratches.

In the above-described embodiment, a metal bump 120 provides an electric connection between the first and second junction pads 107 and 112. The metal bump 120 is formed by dropping melted conductive metal such as gold (Au) in a ball shape on one of the first junction pad 107.

As shown in FIG. 3B, a vibration transfer unit 150A is formed to transfer the sphygmus wave of a human body to the thin film 105. In the present embodiment, the vibration transfer unit 150A is formed by combining the thin film 105 and the central portion of the flexible circuit substrate layer 110 that overlaps the thin film 105. The combination of the flexible circuit substrate layer 110 and the thin film 105 can be achieved in a method such as pressing, heating, ultrasonic welding, chemical junction, and adhesive coating. The formation of the vibration transfer unit 150A is not necessarily performed after the flexible circuit substrate layer 110 is mounted on the substrate layer 102. The vibration transfer unit 150A can be formed at the same time when the flexible circuit substrate layer 110 is mounted on the substrate layer 102, or before the flexible circuit substrate layer 110 is mounted on the substrate layer 102.

The lower surface of the vibration transfer unit 150A contacts the thin film 105 and the upper surface thereof contacts a human body, that is, the wrist 1, to detect the sphygmus wave. Since the flexible circuit substrate layer 110 is formed of an flexible elastic material, the vibration of the radial artery 5 due to the sphygmus wave can be well transferred to the thin film 105. For the improvement of the sensitivity in the vibration transferal, an elastic coefficient of the vibration transfer unit 150A can be lower than that of the shape deformation element of the vibration detection unit, that is, the thin film 105. Since the adhesion layer 130A is formed of a relatively non-elastic and solid material such as cured resin or molding compound, when the adhesion layer 130A is extended to overlap the thin film 105, a sphygmus wave detection performance may be deteriorated. To address this problem, in the present embodiment, the vibration transfer unit 150A is formed by combining the central portion of the flexible circuit substrate layer 110 and the thin film 105 prior to the formation of the adhesion layer 130A.

Although it is not illustrated in the drawings, the vibration transfer unit 150A can further include an outermost layer that directly contacts human skin outside the flexible circuit substrate layer 110. The outermost layer is formed of an elastic material that is harmless to the human body.

Next, a liquid material, for example, resin or molding compound, is implanted between the substrate layer 102 and the flexible circuit substrate layer 110 and heated and cured in an appropriate condition so that the adhesion layer 130A is formed. Since a gap G1 between the flexible circuit substrate layer 110 and the upper surface of the substrate layer 102 is merely tens of micrometers, the gap G1 can be filled with the liquid material by a capillary force. The adhesion layer 130A reinforces the junction force between the substrate layer 102 and the flexible circuit substrate layer 110 and protects the junction portion between the first and second junction pads 107 and 112.

In the contact force sensor package 100A, since the thin flexible circuit substrate layer 110 and the substrate layer 102 are combined to each other, the distance between the radial artery 5 and the thin film 105 can be reduced. Thus, the sensitivity in the detection the sphygmus wave is improved. Also, since the size of the contact force sensor package can be reduced compared to the conventional contact force sensor package in a wire bonding method, the contact force sensor package 100A can be more densely arranged in the blood pressure measuring block 15 of FIG. 2. Thus, when blood pressure is measured by wearing the blood pressure meter 10 of FIG. 2, the possibility of generation of a measurement error is reduced. That is, the blood pressure measuring performance can be improved.

Figure 4A:
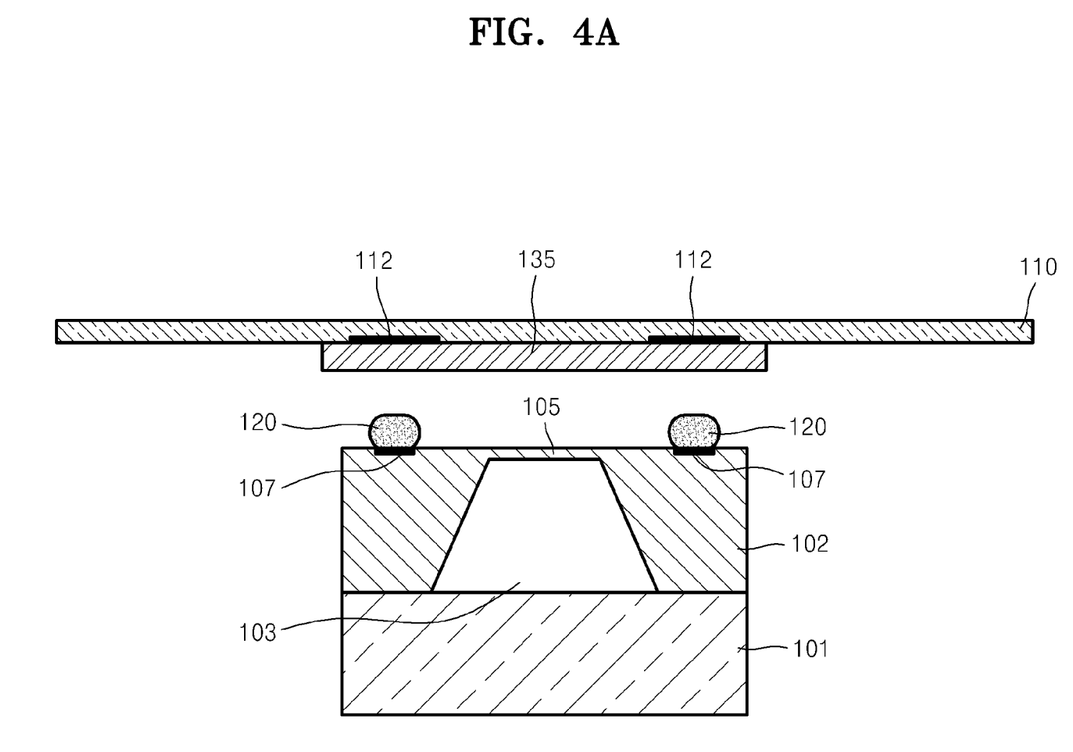
FIG. 4A is a cross-sectional view showing a method for fabricating a contact force sensor package according to another embodiment of the present invention.
Figure 4B:
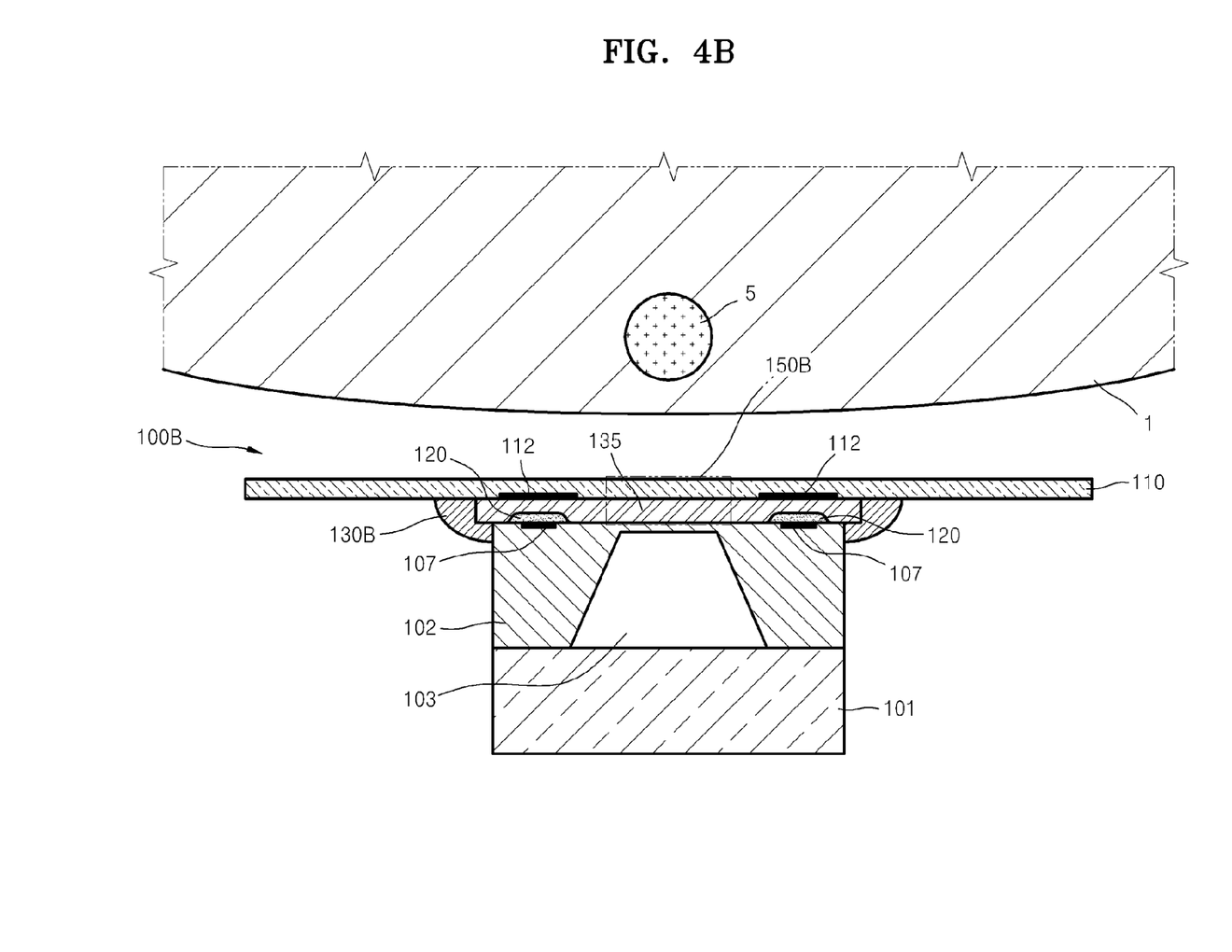
FIG. 4B is a cross-sectional view showing a completed contact force sensor package.

FIG. 4A is a cross-sectional view showing a method for fabricating a contact force sensor package according to another embodiment of the present invention. FIG. 4B is a cross-sectional view showing a completed contact force sensor package which can be applied to the blood pressure meter of FIG. 2 like the contact force sensor package 100A of FIG. 3B. In the following description, the same reference numerals as those of FIGS. 3A and 3B indicate the same constituent elements.

Referring to FIGS. 4A and 4B, the contact force sensor package 100B includes the base layer 101, the substrate layer 102 deposited on the base layer 101 and having the thin film 105, the pair of first junction pads 107, and the cavity 103, the flexible circuit substrate layer 110 mounted on the substrate layer 102 and having the pair of second junction pads 112, and an adhesion layer 130B to reinforce a junction force between the substrate layer 102 and the flexible circuit substrate layer 110.

In the method for fabricating the contact force sensor package 10B, as shown in FIG. 4A, the substrate layer 102 is prepared and deposited on the base layer 101. The metal bump 120 is formed on the first junction pad 107. An anisotropic conductive layer 135 is provided between the flexible circuit substrate layer 110 and the first junction pad 107. The anisotropic conductive layer 135 is of a film type.

As shown in FIG. 4B, the flexible circuit substrate layer 110 presses against the substrate layer 102 such that the lower surface of the central portion of the anisotropic conductive layer 135 can contact the thin film 105 and the upper surface of the anisotropic conductive layer 135 can contact the flexible circuit substrate layer 110. Thus, the first and second junction pads 107 and 112 are electrically connected via the metal bump 120 and the anisotropic conductive layer 135.

At the same time when the first and second junction pads 107 and 112 are electrically connected, a vibration transfer unit 150B to transfer the sphygmus wave to the thin film 105 is formed. The vibration transfer unit 150B includes the central portion of the anisotropic conductive layer 135 contacting the thin film 105 and the central portion of the flexible circuit substrate layer 110 contacting the human body, that is, the wrist 1, to detect the sphygmus wave. Since the anisotropic conductive layer 135 and the flexible circuit substrate layer 110 are all formed of an elastic material, have an elastic coefficient lower than that of the thin film 105, and closely contact each other, the vibration of the radial artery 5 due to the sphygmus wave can be well transferred to the thin film 105.

Next, the liquid material such as resin or molding compound is implanted between the substrate layer 102 and the flexible circuit substrate layer 110 and heated and cured in an appropriate condition to form the adhesion layer 130B. The adhesion layer 130B reinforces a junction force between the substrate layer 102 and the flexible circuit substrate layer 110.

In the contact force sensor package 10B, since the thin flexible circuit substrate layer 110 and the substrate layer 102 are combined to contact each other, the distance between the radial artery 5 and the thin film 105 can be reduced. Thus, the sensitivity in the detection of the sphygmus wave can be improved. Also, since the size of the contact force sensor package can be reduced compared to the conventional contact force sensor package in a wire bonding method, the contact force sensor package 100B can be more densely arranged in the blood pressure measuring block 15 of FIG. 2. Thus, when blood pressure is measured by wearing the blood pressure meter 10 of FIG. 2, the possibility of generation of a measurement error is reduced. That is, the blood pressure measuring performance can be improved.

Figure 5A:
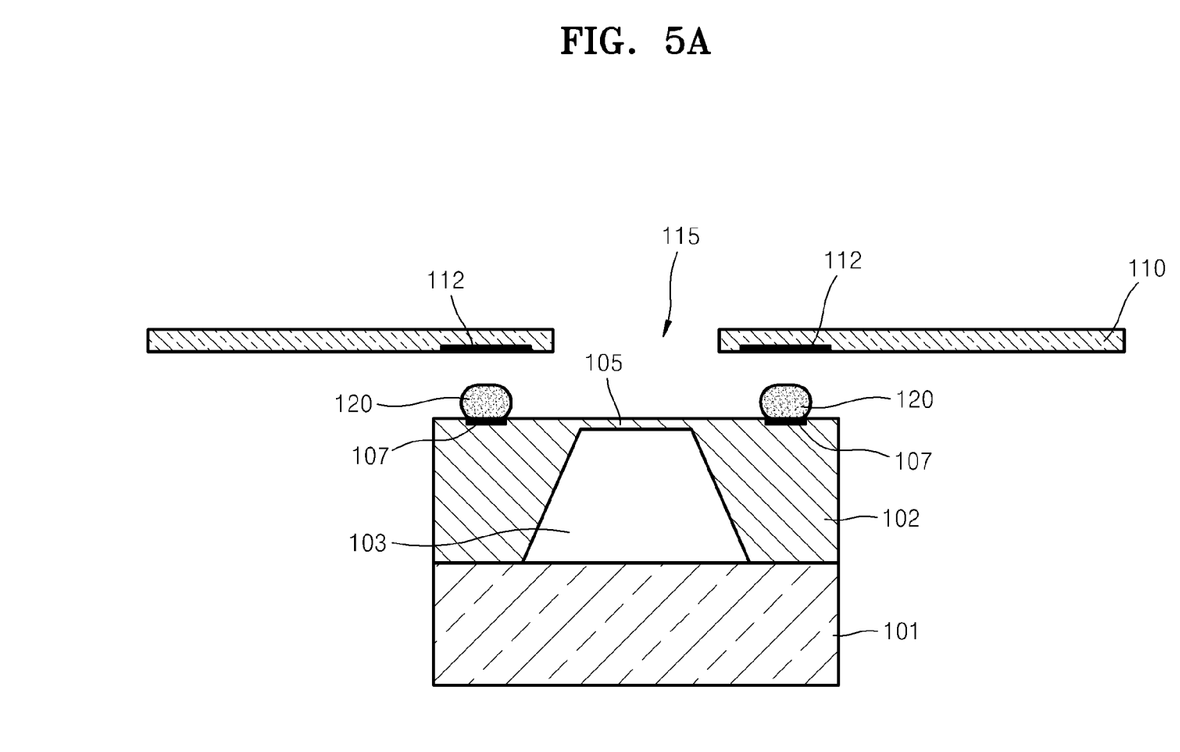
FIGS. 5A and 5B are cross-sectional views sequentially showing a method for fabricating a contact force sensor package according to another embodiment of the present invention.
Figure 5B:
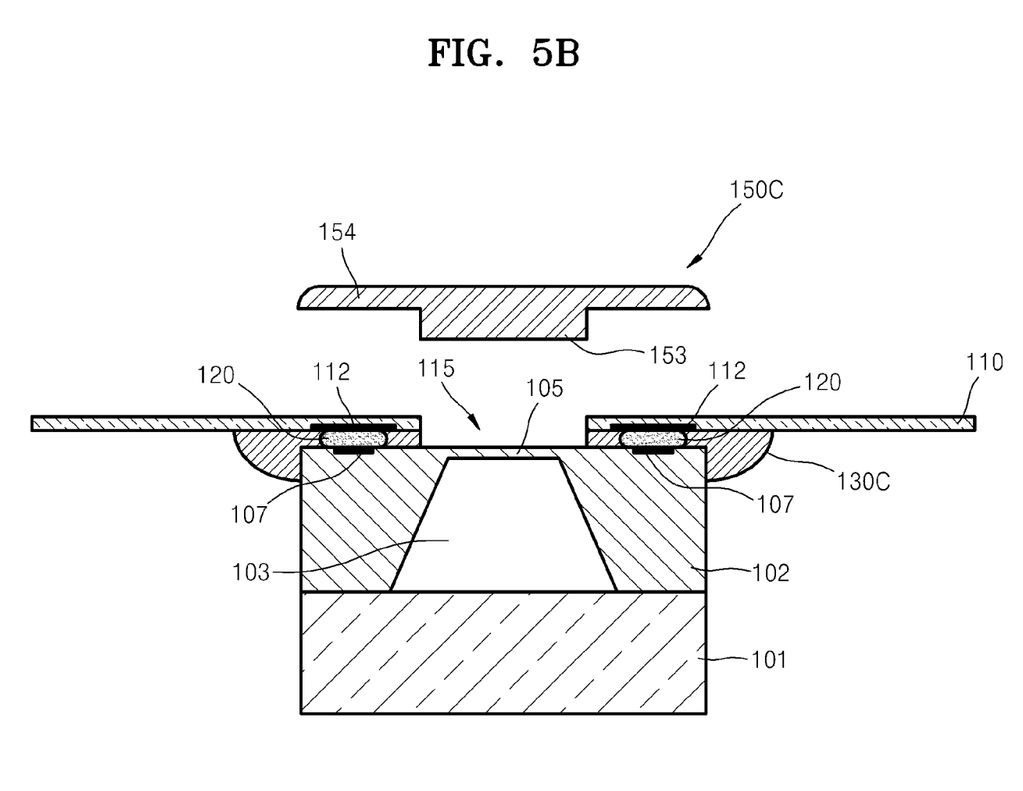
Figure 5C:
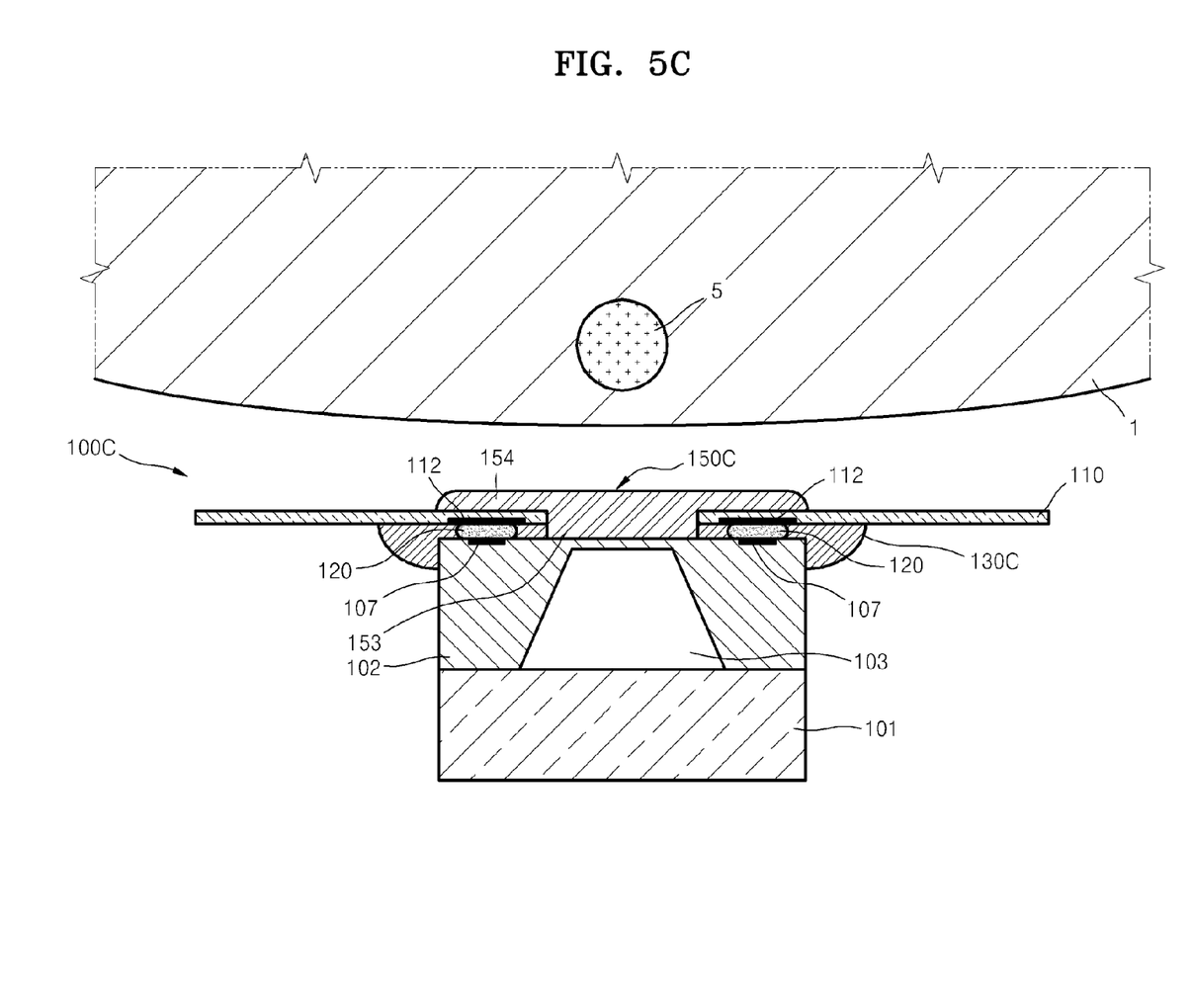
FIG. 5C is a cross-sectional view of a completed contact force sensor package.

FIGS. 5A and 5B are cross-sectional views sequentially showing a method for fabricating a contact force sensor package according to another embodiment of the present invention. FIG. 5C is a cross-sectional view of a completed contact force sensor package which can be applied to the blood pressure meter of FIG. 2 like the contact force sensor packages 100A and 100B shown in FIGS. 3B and 4B. In the following description, the same reference numerals as those of FIGS. 3A and 3B indicate the same constituent elements.

Referring to FIGS. 5A-5C, the contact force sensor package 100C includes the base layer 101, a substrate layer 102 having the thin film 105, the pair of first junction pads 107, and the cavity 103, the flexible circuit substrate layer 110 mounted on the substrate layer 102 and having the pair of second junction pads 112, an adhesion layer 130C to reinforce a junction force between the substrate layer 102 and the flexible circuit substrate layer 110, and a vibration transfer member 150C.

In the method for fabricating the contact force sensor package 100C, as shown in FIG. 5A, the substrate layer 102 is prepared and deposited on the base layer 101. Next, the pair of metal bumps 120 are formed on the pair of first junction pads 107. The flexible circuit substrate layer 110 is pressed against the substrate layer 102 to allow the pair of second junction pads 112 to contact the pair of metal bumps 120, thereby mounting the flexible circuit substrate layer 110 on the substrate layer 102. Accordingly, the first and second junction pads 107 and 112 are electrically connected via the metal bumps 120. Prior to the mounting of the flexible circuit substrate layer 110 on the substrate layer 102, an opening 115 is formed in the flexible circuit substrate layer 110 so that the thin film can be exposed.

Next, after the flexible circuit substrate layer 110 is mounted on the substrate layer 102, as shown in FIG. 5B, a liquid material, for example, resin or molding compound, is implanted between the substrate layer 102 and the flexible circuit substrate layer 110 and heated and cured in an appropriate condition so that the adhesion layer 130C is formed. As it is described above with reference to FIG. 3B, since the gap between the flexible circuit substrate layer 110 and the upper surface of the substrate layer 102 is merely tens of micrometers, the gap can be filled with the liquid material by a capillary force. However, since a portion where the opening 115 is formed cannot be filled with the liquid material due to surface tension, the thin film 105 may still remain exposed.

The vibration transfer member 150C includes an end portion 153 contacting the thin film 105 and a head portion 154 covering the opening 115. A vibration transfer unit is formed by inserting the end portion 153 of the vibration transfer member 150C in the opening 115 after the adhesion layer 130C is formed. In the embodiment shown in FIG. 5C, the vibration transfer unit to transfer the sphygmus wave of a human body to the thin film 105 includes the vibration transfer member 150C. The end portion 153 of the vibration transfer member 150C inserted in the opening 115 contacts the thin film 105 and the head portion 154 contacts the human body, that is, the wrist 1, to detect the sphygmus wave. The vibration transfer member 150C is formed of a material, such as rubber or silicon resin, having an elastic coefficient lower than that of the thin film 105. Thus, the vibration of the radial artery 5 due to the sphygmus wave can be well transferred to the thin film 105.

The contact force sensor package 100C can reduce the distance between the radial artery 5 and the thin film 105 because the thin flexible circuit substrate layer 110 and the substrate layer 102 are combined to closely contact each other. Thus, the sensitivity of the detection of the sphygmus wave is improved. Also, since the size of the contact force sensor package 100C can be reduced compared to the conventional contact force sensor package in a wire bonding method, the contact force sensor package 100C can be more densely arranged in the blood pressure measuring block 15 of FIG. 2. Thus, when blood pressure is measured by wearing the blood pressure meter 10 of FIG. 2, the possibility of generation of a measurement error is reduced. That is, the blood pressure measuring performance can be improved.

Also, since the portion contacting the human body is limited to the vibration transfer member 150C, even when many persons use the single blood pressure meter 10 of FIG. 2, the vibration transfer member 150C only can be separated from the flexible circuit substrate layer 110 and sterilized for reuse which is good for sanitary reasons. Also, a trouble of the flexible circuit substrate layer 110 can be avoided which is good for economical reasons.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A contact force sensor package comprising:
   a substrate layer formed of silicon and having a vibration detection unit that includes a shape deformation element which changes shape by a contact force and a pair of first junction pads that are electrical connection ports which are provided on an upper surface of the substrate layer;
   a flexible circuit substrate layer formed of an elastic material and having a pair of second junction pads provided at a position corresponding to the first junction pads and electrically connected to the first junction pads, via a pair of metal bumps;
   a vibration transfer unit having one side contacting the shape deformation element of the vibration detection unit and the other side contacting a human body to detect a sphygmus wave and transferring the sphygmus wave to the vibration detection unit; and
   an adhesion layer formed between the substrate layer and the flexible circuit substrate layer to reinforce a junction force between the substrate layer and the flexible circuit substrate layer, the adhesion layer being not formed in an area overlapping at least the vibration transfer unit, and wherein the elastic material of the flexible circuit substrate layer has an elastic coefficient which is less than an elastic coefficient of the shape deformation element.

2. The contact force sensor package of claim 1, wherein the elastic material of the flexible circuit substrate layer is a first elastic material and the vibration transfer unit is formed of a second elastic material.

3. The contact force sensor package of claim 2, wherein an elastic coefficient of the second elastic material of the vibration transfer unit is less than an elastic coefficient of the vibration detection unit.

4. The contact force sensor package of claim 1, wherein the vibration transfer unit includes a portion of the flexible circuit substrate layer combined to the vibration detection unit.

5. The contact force sensor package of claim 1, further comprising an anisotropic conductive layer which electrically connects the second junction pads and the pair of metal bumps, wherein the vibration transfer unit includes a portion of the anisotropic conductive layer contacting the vibration detection unit and a portion of the flexible circuit substrate layer contacting the portion of the anisotropic conductive layer.

6. The contact force sensor package of claim 1, wherein the flexible circuit substrate layer includes an opening formed to expose the vibration detection unit, and the vibration transfer unit includes a vibration transfer member provided in the opening, contacting the vibration detection unit, and capable of covering the opening.

7. The contact force sensor package of claim 6, wherein the vibration transfer member is formed of an elastic material.

8. The contact force sensor package of claim 1, wherein the elastic material of the flexible circuit substrate layer is a first elastic material and the vibration transfer unit includes an outermost layer formed of a second elastic material that is harmless to the human body.

9. The contact force sensor package of claim 1, wherein the adhesion layer is formed as a liquid material implanted between the substrate layer and the flexible circuit substrate layer and is cured.

10. The contact force sensor package of claim 1, wherein the shape deformation element has piezoresistance, piezoelectricity, and capacitance, at least one of which measurably varies according to the contact force.

11. The contact force sensor package of claim 10, wherein the shape deformation element is one of a thin film, a cantilever beam, and a bridge.

12. A blood pressure meter comprising:
a blood pressure measuring block having at least one contact force sensor package detecting a sphygmus wave of a human body and measuring blood pressure based on the detected sphygmus wave; and
a contact maintaining device maintaining a state in which the blood pressure measuring block contacts the human body,
wherein the contact force sensor package comprises:
a substrate layer formed of silicon and having a vibration detection unit that includes a shape deformation element which changes shape by a contact force and a pair of first junction pads that are electrical connection ports which are provided on an upper surface of the substrate layer;
a flexible circuit substrate layer formed of an elastic material and having a pair of second junction pads provided at a position corresponding to the first junction pads and electrically connected to the first junction pads, via a pair of metal bumps;
a vibration transfer unit having one side contacting the shape deformation element of the vibration detection unit and the other side contacting a human body to detect a sphygmus wave and transferring the sphygmus wave to the vibration detection unit; and
an adhesion layer formed between the substrate layer and the flexible circuit substrate layer to reinforce a junction force between the substrate layer and the flexible circuit substrate layer, the adhesion layer being not formed in an area overlapping at least the vibration transfer unit, and wherein the elastic material of the flexible circuit substrate layer has an elastic coefficient which is less than an elastic coefficient of the shape deformation element.

13. The blood pressure meter of claim 12, wherein the blood pressure block includes a plurality of the contact force sensor packages and, when one of the contact force sensor packages detects an effective sphygmus wave, blood pressure is measured based on the detected sphygmus wave.

14. A method for fabricating a contact force sensor package, the method comprising:
preparing a substrate layer formed of silicon and having a vibration detection unit that includes a shape deformation element which changes shape by a contact force and a pair of first junction pads that are electrical connection ports which are provided on an upper surface of the substrate layer;
providing a flexible circuit substrate layer formed of an elastic material and having a pair of second junction pads at a position overlapping the first junction pads;
forming a pair of metal bumps which electrically connect the first and second junction pads;
forming a vibration transfer unit having one side contacting the shape deformation element of the vibration detection unit and the other side contacting a human body to detect a sphygmus wave and transferring the sphygmus wave of the human body to the vibration detection unit; and
forming an adhesion layer by implanting and curing a liquid material between the substrate layer and the flexible circuit substrate layer to reinforce a junction force between the substrate layer and the flexible circuit substrate layer, wherein the liquid material is not implanted in an area overlapping the vibration detection unit, and wherein the elastic material of the flexible circuit substrate layer has an elastic coefficient which is less than an elastic coefficient of the shape deformation element.

15. The method of claim 14, wherein the elastic material of the flexible circuit substrate layer is a first elastic material and the vibration transfer unit is formed of a second elastic material.

16. The method of claim 14, wherein the forming of the vibration transfer unit includes combining a portion of the flexible circuit substrate layer to the vibration detection unit.

17. The method of claim 14, wherein the forming the pair of metal bumps which electrically connect the first and second junction pads and the forming of the vibration transfer unit are simultaneously performed, and the method further comprises:
providing an anisotropic conductive layer between the flexible circuit substrate layer and the substrate layer, such that the anisotropic conductive layer is electrically connected to the second junction pads and the pair of metal bumps; and
pressing the flexible circuit substrate layer against the substrate layer to allow one side of the anisotropic conductive layer to contact the vibration detection unit and the other side of the anisotropic conductive layer to contact the flexible circuit substrate layer.

18. The method of claim 14, further comprising forming an opening in the flexible circuit substrate layer to expose the vibration detection unit, wherein the forming of the vibration transfer unit comprises providing a vibration transfer member in the opening that is capable of contacting the vibration detection unit and covering the opening.

19. The method of claim 18, wherein the elastic material of the flexible circuit substrate layer is a first elastic material and the vibration transfer member is formed of a second elastic material.

* * * * *